(12) United States Patent
Thompson et al.

(10) Patent No.: US 6,663,610 B1
(45) Date of Patent: Dec. 16, 2003

(54) SMOKE EVACUATION SYSTEM

(75) Inventors: Barry M. Thompson, Maple Grove, MN (US); Jeffrey K. Drogue, Minneapolis, MN (US)

(73) Assignee: Leonard S. Schultz, M.D., St. Louis Park, MN (US)

( * ) Notice: Subject to any disclaimer, the term of this patent is extended or adjusted under 35 U.S.C. 154(b) by 47 days.

(21) Appl. No.: 09/710,288

(22) Filed: Nov. 10, 2000

Related U.S. Application Data

(63) Continuation-in-part of application No. 09/673,406, filed as application No. PCT/US99/08207 on Apr. 15, 1999.
(60) Provisional application No. 60/082,125, filed on Apr. 17, 1998.

(51) Int. Cl.[7] .................................................. A61M 1/00
(52) U.S. Cl. ........................ 604/313; 604/35; 604/128; 604/317
(58) Field of Search ..................... 95/273, 286; 604/22, 604/27, 35, 313, 315, 317, 128; 606/115; 128/912; 44/385.1, 486, 413

(56) References Cited

U.S. PATENT DOCUMENTS

| 4,692,140 | A | * | 9/1987 | Olson ........................ 604/119 |
|---|---|---|---|---|
| 4,764,165 | A | * | 8/1988 | Reimels et al. ................ 604/22 |
| 4,921,492 | A | * | 5/1990 | Schultz et al. ............... 128/888 |
| 5,015,243 | A | * | 5/1991 | Schifano ..................... 604/315 |
| 5,226,939 | A | * | 7/1993 | Nicolas et al. ................. 55/309 |
| 5,234,428 | A | * | 8/1993 | Kaufman ...................... 604/35 |
| 5,674,219 | A | * | 10/1997 | Monson et al. ................ 604/22 |
| 5,722,949 | A | * | 3/1998 | Sanese ........................ 604/119 |
| 5,868,722 | A | * | 2/1999 | Yeh et al. ..................... 604/313 |
| 5,941,873 | A | * | 8/1999 | Korenfeld .................... 604/313 |
| 6,110,259 | A | * | 8/2000 | Schultz et al. .............. 55/385.1 |

OTHER PUBLICATIONS

Mangram AJ, Horan TC, Pearson ML, Silver LC, Jarvis WR. *Special Articles: Guidelines for Prevention of Surgical Site Infection, 1999.* AJIC 1999 Apr.; 27(2):97–118, 110–111, 118.

Enggaard TP, Moller–Larsen F. *Influenece of local air suction on the density of air–borne bacteria during cementation of alloplasties.* Ugeskr Laeger Feb. 10, 1997; 159(7):952–5, National Library of Medicine www.ncbi.nlm.nih.gov.

Friberg B. *Ultraclean laminar airflow ORs,* AORN J 1998 Apr.; 67(4):841–2, 845–51, National Library of Medicine www.ncbi.nlm.nih.gov.

Friberg BE, Friberg S, Burman LG. *Zoned vertical ultraclean operating room ventilation. A novel concept making long side walls unnecessary.* Acta Orthop Scand 1996 Dec.; 67(6):578–82, National Library of Medicine www.ncbi.nlm.nih.gov.

Cornet M, Levy V, Fleury L, Lortholary J, Barquins S, Coureul MH, Deliere E, Zittoun R, Brucker G, Bouvet A. *Efficacy of prevention by high–efficiency particulate air filtration or laminar airflow against Aspergillus airborne contamination during hospital renovation.* Infect Control Hosp Epidemiol 1999 Jul.; 20(7):508–13, National Library of Medicine www.ncbi.nlm.nih.gov.

* cited by examiner

*Primary Examiner*—Weilun Lo
*Assistant Examiner*—Michael Bogart
(74) *Attorney, Agent, or Firm*—Dorsey & Whitney LLP

(57) ABSTRACT

An improved smoke evacuation system and method for removing gaseous byproducts of surgical procedures and noxious vapors from chemicals is provided. The smoke and vapor evacuation system includes a vacuum head positionable at a surgical site or incorporated into a workstation. The vacuum head includes a plenum, and a plenum support for preventing the plenum from collapsing when a vacuum or low pressure is established therein, and is adapted to facilitate the use of the system in a variety of surgical or commercial procedures at a variety of surgical sites or commercial workstations.

44 Claims, 16 Drawing Sheets

SMOKE EVACUATION SYSTEM

PRIORITY

The present application is a continuation-in-part of U.S. patent application Ser. No. 09/673,406, filed Mar. 29, 2002, which is a 35 USC 371 application based on international application number PCT/US99/08207 filed Apr. 15, 1999, which claims the priority of U.S. provisional patent application No. 60/082,125 filed Apr. 17, 1998.

BACKGROUND

This invention relates to equipment, systems and methods for the removal of gaseous and/or substantially gaseous material. Such material includes, but is not limited to aerosol and particle byproducts of surgical procedures and any procedures involving cutting, heating or burning, such as odors from chemicals, ultrasonic vapors, and ion dust particles. More particularly, the present invention relates to an evacuator or vacuum head for an evacuation system that efficiently removes smoke, vapor, or plumes released by chemicals or produced by the use of lasers, sonic cutting and/or cautery or other surgical techniques or instruments at a surgical site.

Heating and/or burning of tissue during surgical procedures has become commonplace. An unwanted byproduct of such heating and/or burning, however, is the smoke generated thereby. Smoke plumes can obscure the surgeon's field of vision and the odor generated is unpleasant and distracting to the entire surgical team and to the patient, if awake. Moreover, the smoke plume may contain infectious agents that present a danger to persons in the operating room, and which can leave a lingering contamination within the operating area. Chemical vapor (e.g., such as that produced by the cleaning of computer parts) is, likewise, irritating to the respiratory tract of those who inhale it and may be carcinogenic.

Smoke evacuation and filtering systems have been developed to remove smoke plumes from surgical sites and chemical vapors from the work environment. Such systems typically include a hose connected to a vacuum source or generator and a suction wand connected to the hose, that is, placed at the site where the aerosol is generated. Various filtration systems have been used in conjunction with such vacuum generators to remove odor and infectious agents. Typically, the wand and hoses of known evacuation and filtration systems have required the constant attention or activity of an attendant to hold the wand or the nozzle of the hose close to the surgical site. Another problem is that the flow of air through the hose nozzle and the suction motor are sources of excessive and unwanted noise in the operating room or at the workstation.

More recently, at least in part to address the problems with wands, smoke evacuation systems may include an end effector that can be held in place at a surgical site without the constant attention of a nurse or other attendant. At least one such evacuation system and end effector is disclosed in U.S. Pat. No. 4,921,492 (Schultz et al.), the disclosure of which patent is incorporated herein by reference. Schultz et al. disclose an end effector for removing the gaseous byproducts of laser surgery from a surgical site. The end effector includes a flexible hose and a pliable vacuum head adhesively attachable in a substantially airtight relationship around a surgical site. The vacuum head includes a generally annular plenum for drawing plumes away from the surgical site from around a 360° arc. A porous plenum support prevents the flexible plenum from collapsing in the presence of a vacuum, and diffuses the vacuum around the entire periphery of the plenum.

U.S. Pat. No. 5,015,243 (Schifano) discloses another smoke evacuator including a flexible suction head for surrounding an operative site to draw smoke and air from around a perimeter of the site as smoke is produced. In one embodiment, the suction head is a doughnut shaped tubular member including a plurality of radial openings on an interior surface of the tubular member that faces the operative site. Schifano teaches that the tubular ring member may be circular or oval, and that it need not completely surround the operative site as long as air is drawn substantially in a surrounding fashion.

Another problem faced during operations is surgical site infection. Surgical site infections account for a large number of nosocomial infections. These types of infections occur when bacteria from the operating area enters a surgical site. Surgical site infections can increase the probability of death, and can increase a patient's hospital stay and cost. An article entitled "Guideline For Prevention of Surgical Site Infection, 1999", published in the *American Journal of Infection Control*, May 1999, pp.97–118 (Mangram, Alicia J. et al.), the disclosure of which article is incorporated herein by reference, presents recommendations for preventing these types of infections. The article suggests that one way to control surgical site infections is to improve operating room ventilation. The article discloses that a laminar airflow, designed to move particle-free air (which may be known as "ultraclean air" or like) over the aseptic operating site at a velocity of around 0.3–0.5 $\mu$m/second, effectively sweeps particles out of its path, and reduces surgical site infections following operations by more than 50%. Combining the laminar airflow of ultra-clean air over a surgical site with a smoke evacuation system could increase the safety and comfort for the operating room staff and the patient.

While smoke evacuation systems and end effectors of the Schultz et al. and Schifano type are well-suited for their intended purposes, there is room for improvement. For example, while the end effectors are pliable or flexible to conform to a surface to which they are attached, neither discloses a skeletal stiffening structure or frame for helping to maintain a conformed shape. Such a skeleton or frame would be valuable to adapt end effectors or vacuum heads for smoke evacuation for use on or near irregular physical features such as, for example, the ear, nose, mouth, or in the area of joints. It would also be advantageous if the generally central, site access opening of such end effectors could be selectively varied in size to accommodate different sizes of incisions and different procedures, and if end effectors could be made available with the intake opening or openings in various locations, so that a particular end effector could be selected depending on the procedure to be performed. It would be advantageous if end effectors were available in a generally elongated, tubular shape bendable into a selected configuration by the user, and wherein the shaped or bent effectors would tend to remain in the selected configuration. It would be advantageous if a blower station and vacuum station could be set up and connected to an end effector in order to create and/or supply and evacuate a laminar airflow of ultra-clean air across a surgical site, and/or to do so in conjunction with filtration. It would also be advantageous if an end effector or vacuum head could be integrated with the widely used customary surgical drapes or drape material, or incorporated into part of a workstation that would contain noxious chemical fumes.

SUMMARY

The present invention provides an evacuator well-suited for removing or evacuating smoke, chemical vapors, aerosols, gaseous or generally gaseous material and fluids, including fluids with entrained particles or other material. It is well-suited for use in removing such substances from surgical sites, workstations and manufacturing assemblies or processing sites.

The needs outlined above are in large measure solved by a smoke evacuation system and method, including an evacuator, in accordance with the present invention. The embodiments described herein are designed to efficiently and quietly remove smoke or other aerosols, including smoke or bioaerosols generated during surgical procedures, and can be used at a surgical site without constant attention or manipulation by the surgeon or an attendant. They would also remove vapor from the work site.

An improved smoke evacuation system and method for removing gaseous byproducts of surgical or commercial procedures is provided by the present invention. The smoke evacuation system includes a vacuum head positionable at a surgical or other work site. The vacuum head includes a plenum, and a plenum support for preventing the plenum from collapsing when a vacuum or low pressure is established therein, and is adapted to facilitate the use of the system in a variety of surgical procedures at a variety of surgical sites.

In one embodiment, the present invention comprises a vacuum smoke evacuator head for coupling to a vacuum source for withdrawing generally gaseous byproducts, including smoke, fine particulate matter, air and the like, from a surgical or commercial site. The smoke evacuator head is substantially made of a generally pliable or flexible material and defines a plenum. A plenum support is carried within the plenum to provide support to the plenum and to prevent the plenum from collapsing when a vacuum or relatively low pressure area is established therein. The smoke evacuator head includes an open intake facing and/or intake openings, and may be positioned adjacent to or in a surgical site. An adhesive may be carried by the head for maintaining it in a selected position or location relative to the surgical site.

In one embodiment, the smoke evacuator head includes at least one access opening which may be selectively expanded in size. Typically, the access opening may be generally centrally located in the vacuum head, and has an initial peripheral edge which may be moved generally concentrically outwardly by selectively removing one or more removable, generally concentric peripheral portions extending substantially around the opening. Also typically, the opening, whether the initial size or one of the expanded sizes, may be covered or sealed before use by a removable film.

In another embodiment, the smoke evacuator vacuum head includes a skeletal stiffening member or positioning frame whereby the head may be configured and tends to remain in the selected configuration. The skeletal structure may comprise a single, flexible elongated member formed of a suitable material which may be bent or twisted, yet has sufficient rigidity to retain the selected bend or twist. The skeletal structure may be internal or external, and may comprise a single, elongated member, a single annular member, a plurality of axially aligned members, a number of parallel and/or branch members or a combination thereof. This embodiment may be well-suited for use in regions of the body having rather irregular surfaces such as joints, the ear, nose or mouth.

In another embodiment, the smoke evacuator may comprise a generally tubular body having two ends, one of which is adapted to be connected to another smoke evacuator vacuum head or to a coupling, such as a hose, for operably coupling the tubular body to a vacuum source. The other end may be free. The body may have one or more regions comprising openings or an open facing for admitting smoke and the like when a vacuum or low pressure is established in the body. In this embodiment, the body may have a stiffening element or a skeletal structure to allow the body to easily bend and remain in a particular shape for use in different situations. This embodiment of the vacuum head may be well-suited for use, as an adjunct or alone, in deep incisions or wounds during surgical procedures.

In yet another embodiment, the smoke evacuator vacuum head forms a plenum including a substantially open facing portion for being positioned generally adjacent to a smoke or aersol producing site. In one embodiment, wherein the plenum has a top, outwardly facing wall, is generally annular and includes a generally central access opening, the periphery of the opening being formed by an inner wall, the open facing may be formed in and/or adjacent to the inner wall comprising, for example, a bevel and/or a portion of the top wall. This embodiment is well-suited for use in surgical procedures during which a flap or ridge of skin or tissue may be formed, for example, around or as a result of the incision. Such procedures include plastic surgery procedures and mastectomies, for example, where the vacuum induced in the plenum may tend to pull skin flaps or tissue into it, particularly when the skin flap or tissue is held straight up.

In another embodiment, the evacuation system of the present invention comprises an evacuation hose for detachably connecting a vacuum generator or source and a vacuum head that generally surrounds a surgical site. The vacuum head is substantially made of a generally pliable or flexible material and defines a plenum having a generally central opening. A porous plenum supporting material is carried within the plenum to provide a degree of rigidity to the plenum and to prevent the plenum from collapsing when a vacuum or relatively low pressure area is established therein. The plenum includes an open facing region adjacent to the central opening. An adhesive may be carried by the skin contacting wall of the vacuum head for maintaining the vacuum head in place at a surgical site.

An embodiment and feature of the present invention is the concept of a foam supported channel of selectable cross-sectional area incorporated or integrated with a surgical drape, wherein the channel may be used to convey smoke and/or other aerosol debris away from a surgical site.

Any of the embodiments of the smoke evacuation system or vacuum head described herein may be provided in sterile form and in a color acceptable in an operating room environment.

In one embodiment, the smoke evacuation system of the present invention comprises a vacuum head end effector including generally contiguous, concentric areas or regions, which may be oval, formed or separated by generally concentric perforations whereby the areas may be selectively removed to correspond with required length of an incision or procedural area.

In one embodiment, the end effector in accordance with the present invention would have a pre-provided generally central and oval cutout of specific predetermined dimensions, the purpose of which would be to form a primary or initial work area, and to more easily allow the surgeon or attendant to remove surrounding peripheral oval sections to expand the original opening.

In one embodiment, each removable section of the vacuum head may be provided with a paper backed adhesive running on one surface of the sections. The paper backing would be removed once the size of the field or work area is determined, thereby allowing the remaining portion of the vacuum head and/or drape to affix to the patient's prepped skin or to the medical drape covering the intended site of the surgery.

In one embodiment, the end effector would have suitable connectors, nozzle adapters, and/or connection features, e.g., to allow for simultaneous coupling to both a source of selected fluid or gas, e.g., ultra-clean air, and a source of low pressure or vacuum. In this embodiment, the end effector would provide a unidirectional, laminar airflow over the work site. The end effector includes a plenum having a central opening, a plenum support for preventing the plenum from collapsing when an airflow or a vacuum or low pressure is established therein, and is adapted to facilitate the delivery of, e.g., ultra-clean air across the generally central opening of the head.

In some embodiments, one or more manifold-like connection handles or tubes would extend from the foam filled channel or vacuum head to deliver an airflow and/or to convey the smoke and vapor mixture from the operative site into a conduit and then to a collection, filtration and/or deodorization device wherein the mixture may be processed and the air may be returned to the room.

In some embodiments, the skin of the drape may cover the end effector, the manifold and the drape in continuity. In these and other embodiments, the manifold(s) may be provided to include either straight, i.e., parallel, and/or curved extension lips or walls that extend into or on either side of the plenum support that supports the outer walls of the plenum or evacuator vacuum head. The purpose of these lips or walls would be to prevent the possible kinking, narrowing or other form of occlusion by the covering skin of the drape at the plenum support/ manifold interface or junction. This occlusion might be caused by the downward force placed on the manifold by the attached tubing that usually trails or falls to the floor of the operating room. In some instances, when suction or reduced pressure is applied without the lip extensions in place, the skin can invaginate and cover the entrance orifice of the manifold.

Another embodiment includes a chamber or gathering site for the evacuated smoke as it leaves the foam-filled channel or the plenum toward the exit site of the manifold or connection nozzle. The chamber is attached to the lip extensions or walls (described in the previous paragraph) at one end and forms or is attached to an exit port at the other end. The chamber and/or exit port may be adapted to increase flow velocities by including an area of decreased cross-sectional area. The exit port from which the smoke mixture leaves the smoke evacuator may be coupled to a typical conduit or hose.

Any of the embodiments disclosed herein may be formed by a wall or skin which may be made of the same as the material of a surgical drape. The skin may or may not be fire retardant or resistant, and any of the embodiments may be preferably composed of bio-compatible material and be capable of disposition as such materials are typically disposed of.

It should be appreciated that features of any of the embodiments of the present invention may be selectively combined to adapt the smoke evacuator vacuum head for a variety of situations and surgical procedures.

Other features and advantages of the smoke evacuation device and method of the present invention will become more fully apparent and understood with reference to the following description and appended drawings and claims.

DETAILED DESCRIPTION

The accompanying Figures and this description depict and describe embodiments of the smoke evacuation system and method of the present invention, including the smoke evacuator vacuum head, and features and components thereof. As used herein, the terms "evacuator", "smoke evacuator", "end effector", "vacuum head" and like terms are intended to encompass a structure or structures into which gaseous or generally gaseous or particulate material, such as aerosols, smoke or vapor, may be introduced or be drawn from when the structure is operably coupled to a source of low pressure or vacuum. Such a structure or structures may be placed generally adjacent to a site producing a gaseous or generally gaseous material. As used herein the term surgical field is intended to encompass places where an incision is to be made in the skin or where other surgical operations or procedures are performed or to be performed. With regard to fastening, mounting, attaching or connecting the components of the present invention to form the device and system as a whole, unless specifically described otherwise, such are intended to encompass conventional fasteners such as machine screws, nut and bolt connectors, machine threaded connectors, snap rings, hose clamps such as screw clamps and the like, rivets, nuts and bolts, toggles, pins and the like. Components may also be connected by adhesives, glues, heat sealing, snap fitting, welding, ultrasonic welding, and friction fitting or deformation, if appropriate. Unless specifically otherwise disclosed or taught, materials for making components of the present invention may be selected from appropriate materials such as metal, metallic alloys, natural and manmade fibers, vinyls, plastics and the like, and appropriate manufacturing or production methods including casting, extruding, molding and machining may be used.

Any references to front and back, right and left, top and bottom and upper and lower are intended for convenience of description, not to limit the present invention or its components to any one positional or spacial orientation.

Figure 1:
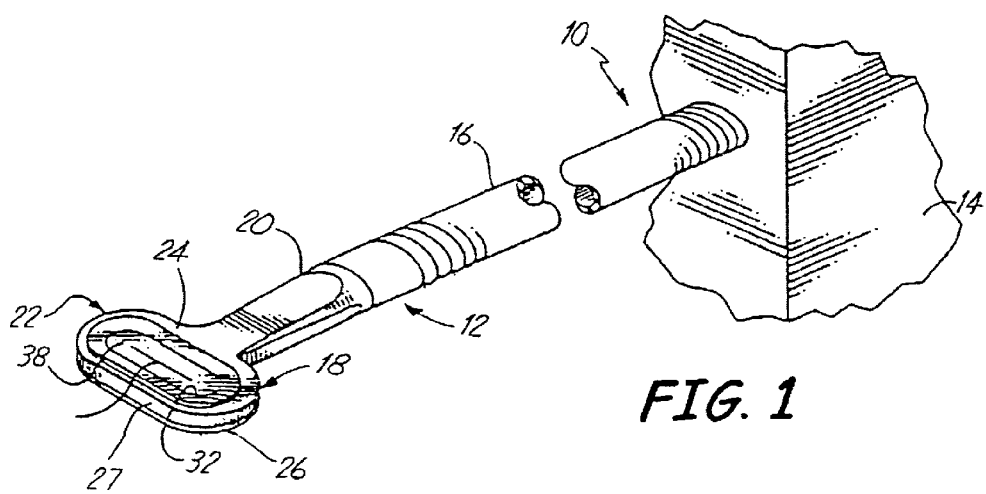
FIG. 1 is a fragmentary, perspective view of a smoke evacuation system including an vacuum head end effector.
Figure 2:
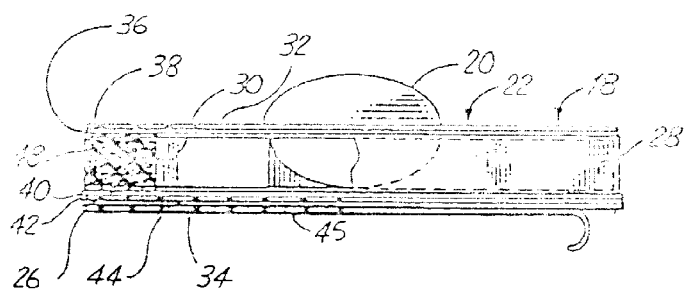
FIG. 2 is a front elevational view of the end effector shown in FIG. 1, with parts broken away for clarity.

Referring to FIGS. 1 and 2, a smoke evacuation system 10 in accordance with the above-noted Schultz et al. patent is depicted. The system includes an end effector 12 detachably connected to a suitable vacuum generator and filtration assembly 14. In one embodiment, the end effector 12 may include a flexible hose 16 coupled to a vacuum head 18 by a generally tubular manifold-like handle 20. In one embodiment, the vacuum head 18 includes a generally flat body 22 having a top wall 24, bottom wall 26 and outer sidewall 27 extending between the top wall 24 and bottom wall 26. The body 22 is preferably formed from a nonporous, pliable synthetic resin so that it will conform to the surface surrounding the surgical site. The top, bottom, and side walls 24, 26, 27 together substantially define a generally annular, internal plenum 28. The walls form an outer skin of the plenum 28 and may be composed of a medical grade, pliable, substantially non-porous material. The material of choice may be a synthetic, or it may be a natural material, such as fibrous material, e.g., cellulose or cotton fiber based material, such as presently used in surgical drapes and/or towels. The material of choice may be with or without flame-retardant characteristics. Preferred synthetic materials may be selected from open-celled foams, urethane film, spun lace polyester, nonwoven polyurethane tape and the like.

The top wall 24 includes an access aperture 32, and the bottom wall 26 includes an access aperture 34, typically, but not necessarily, aligned and/or substantially congruent with the top wall access aperture 32. Preferably, a layer or adhesive 36 is carried by the top wall 24, and a clear film 38 is removably carried in place over the top access aperture 32 by the adhesive 36. Preferably, the bottom wall 26 includes a first adhesive layer 40 and a clear film 42 removably carried by the first adhesive layer 40. A second adhesive layer 44, which may have an antiseptic embedded therein, is carried by the bottom wall clear film 42. A sterile, peel-off shield 45 is removably carried by the antiseptic adhesive layer 44.

It will be appreciated that, upon application of a vacuum to the body 22, the top and bottom wall 24, 26 would be urged together, thereby reducing the volume of the plenum 28. Therefore, in the end effector 18 depicted in FIGS. 1 and 2, and in the embodiments of the invention described herein, an inner core plenum support 48 formed from a porous material such as foam urethane, or another appropriate reticulated, open-cell foam material, a supporting matrix, or the like, may be carried within plenum 28, to provide the body 22 with some rigidity without substantially detracting from the flexibility of the vacuum head 18. The inner core 48 comprises an inner plenum supporting structure 48 that permits the flow of air and smoke into the plenum 28 while blocking the ingress of larger materials such as tissue or surgical materials. Preferably, the inner core support 48 should be made of a synthetic or natural material that is hydrophobic so that it will resist absorption of fluids often present in the operative field. A reticulated open cell foam of a size between 5 and 25 pores per inch (ppi) is well-suited for the inner core. In another embodiment, the plenum support core 48 may be molded and/or may be formed contiguously with the outer skin, and may be provided with a plurality or matrix of airflow shafts or channels.

Whether the shape of vacuum head 18 is generally circular, generally oval or a different shape, in some embodiments, it will be noted that the plenum 28 provides for evacuation of generally gaseous material substantially around a complete 360° arc.

Figure 3:
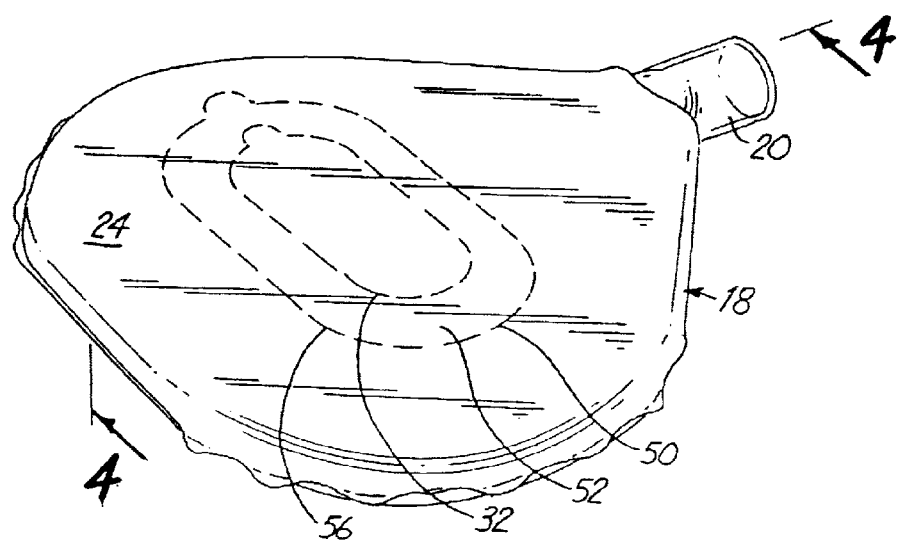
FIG. 3 is a top perspective view of an embodiment of the end effector vacuum head in accordance with the present invention.
Figure 4:
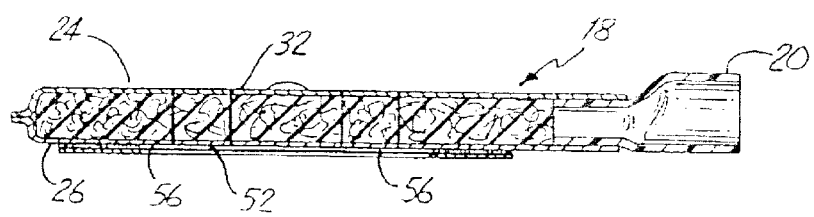
FIG. 4 is a side elevational view of the end effector vacuum head depicted in FIG. 3.

FIGS. 3 and 4 depict an embodiment of the smoke evacuator 18 of the present invention, wherein the central access aperture 32 is expandable to form a larger size aperture or opening 50 by removing a peripheral portion 52 of the evacuator vacuum head 18 from around the originally provided access aperture 32. The top and bottom walls 24, 26 and the plenum support material 48 may include a line of weakness 56, be scored, cut or partially cut to define the removable portion 52 and to facilitate its removal. A selected number of generally concentric or shaped removable portions may be provided. The line of weakness, scoring, cut or perforations 56 may be substantially concentric and congruent with respect to the initial access aperture 32, or they may be adapted to expand the initial access aperture in a selected direction or into a selected shape, e.g., they may comprise one or more arcs or lines of weakness beginning and ending at the peripheral edge of the access opening (see, for example, lines of weakness a and b shown in FIG. 6). (In describing this and other embodiments, features in common with the end effector depicted in FIGS. 1 and 2, and with other embodiments of the invention, are and will be commonly referenced.)

Figure 5:
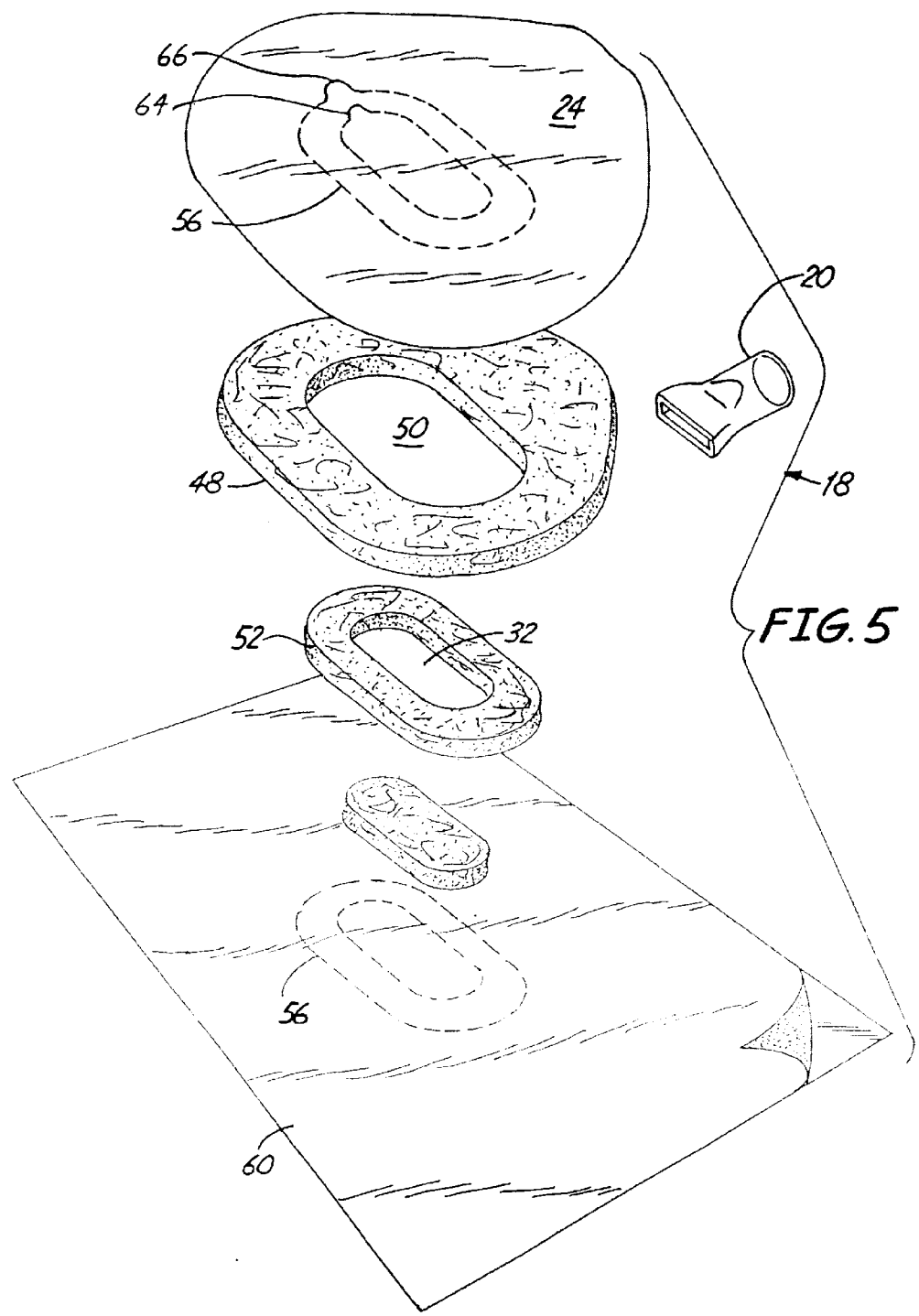
FIG. 5 is an exploded perspective view of another embodiment of the present invention.
Figure 6:
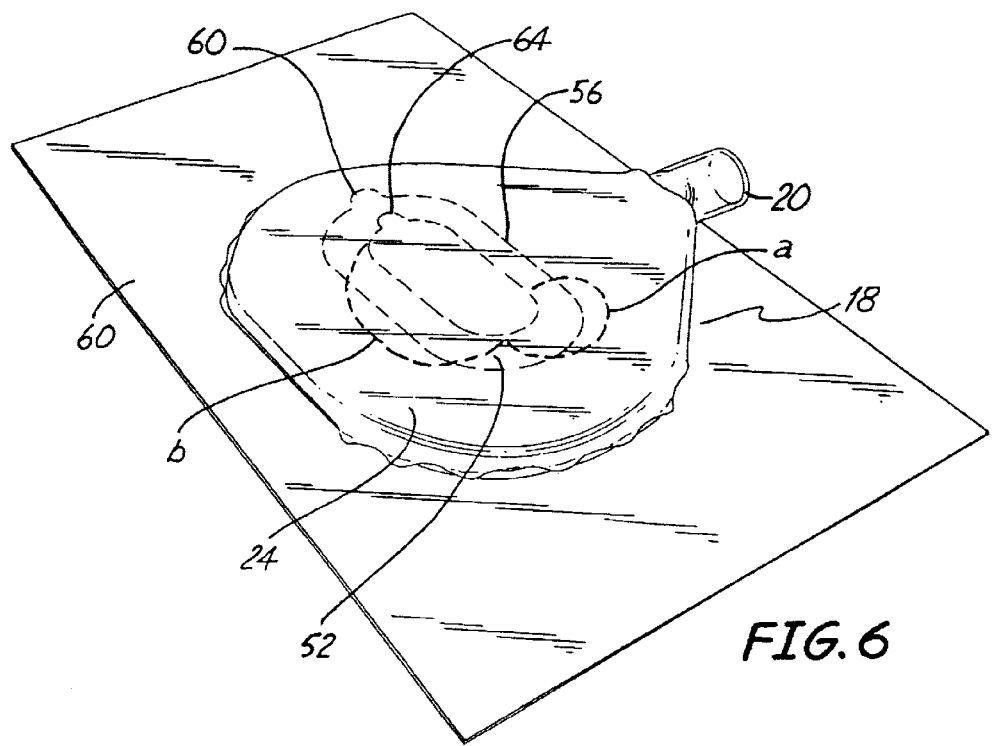
FIG. 6 is a perspective view of the embodiment depicted in FIG. 5.
Figure 12:
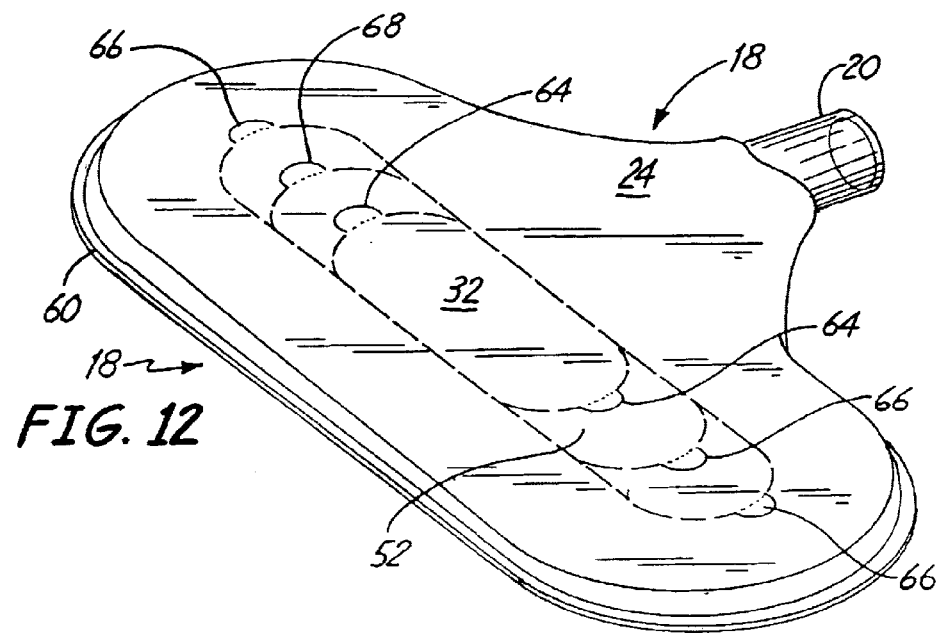
FIG. 12 is a perspective view of another embodiment of the present invention.

FIGS. 5, 6 and 12 depict another embodiment of the smoke evacuator vacuum head 18 of the present invention, wherein the vacuum head 18 is provided with a variable size access aperture, and is integrated with a surgical drape 60 comprising a relatively large, flexible, generally cloth-like sheet material. Such a drape or drapes are widely used to establish or set off a surgical field, may or may not be generally transparent, and may be formed by a polypropylene material or the like, such as PVC or combinations of polypropylene and cellulose. They may carry an adhesive on one surface for connection to the skin of a patient, typically, four strips of adhesive to define a periphery. One surface of the drape may have an adhesive thereon for attachment to the vacuum head end effector 18. Integration of the vacuum head end effector 18 of the present invention may be accomplished by providing a drape or piece of drape material with an opening, placing the end effector 18 over the opening, and attaching or sealing the edges of the end effector 18 to the drape (see FIG. 6). The bottom wall of the end effector 18 may be omitted, in which case the top or outside side wall 24 may be joined to the drape, whereby the drape forms the bottom wall, completing the plenum 28 and encompassing the open-cell, reticulated foam forming the plenum support 48. In use, the integrated drape and end effector 18 may be placed over an intended incision site with the access opening aligned with the site. A tab 64 may be grasped and pulled to permit access to the site. If a larger incision site opening is required initially, or if the incision site needs to be expanded or extended, another tab 66 may be grasped and pulled to remove a peripheral portion 52, thereby enlarging, specifically lengthening, the opening. As depicted in FIG. 12, the pre-cut access opening covering is provided with as many tabs as convenient to facilitate grasping and pulling the covering away from the end effector 18. Pulling one of the tabs releases the pre-perforated covering skin and allows the pre-cut foam 48 to be removed.

Figure 7:
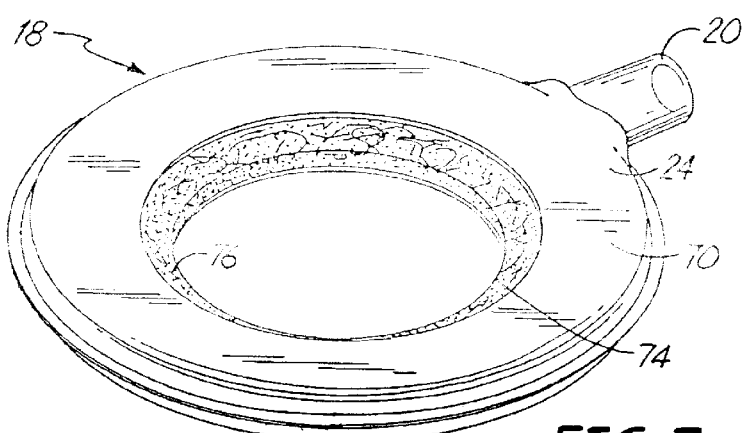
FIG. 7 is a perspective view of another embodiment of the present invention.

FIG. 7 (and others, including FIGS. 13–16) depict another embodiment of the present invention wherein a wire-like skeletal member 70 is provided. The skeletal member 70 is flexible and bendable to the degree that it may be manipulated, bent or twisted into a desired shape, yet it is inflexible or rigid enough to retain its bent or twisted shape. It may be located in the plenum 28 as shown, or it could be appropriately secured to the exterior of the end effector 18.

Figure 8:
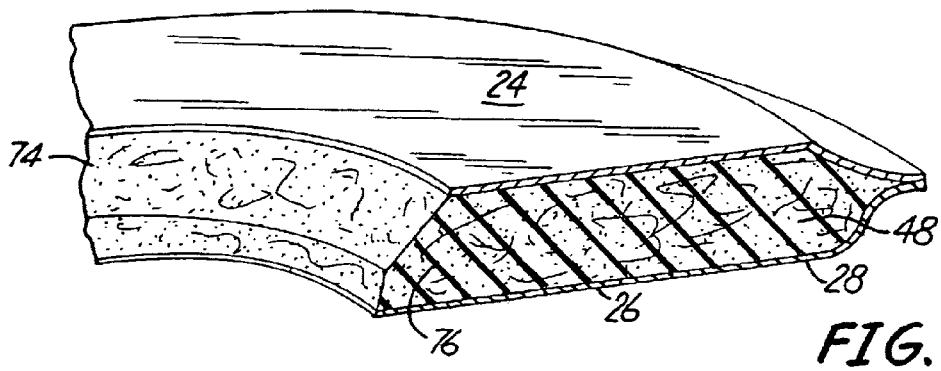
FIG. 8 is a fragmentary perspective view of another embodiment of the present invention.
Figure 9A:
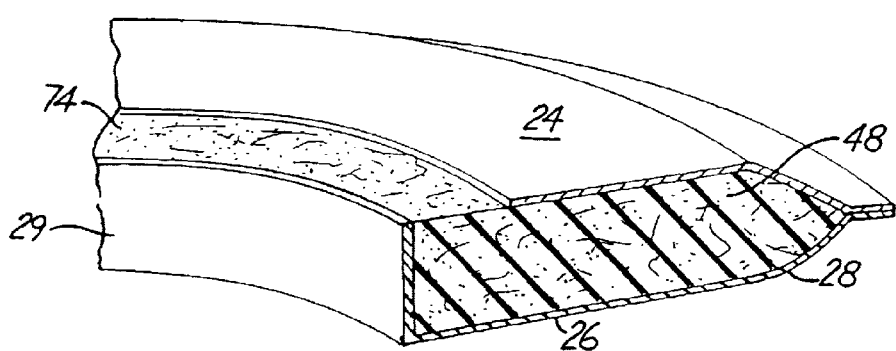
FIG. 9a is a fragmentary perspective view of another embodiment of the present invention.
Figure 9B:
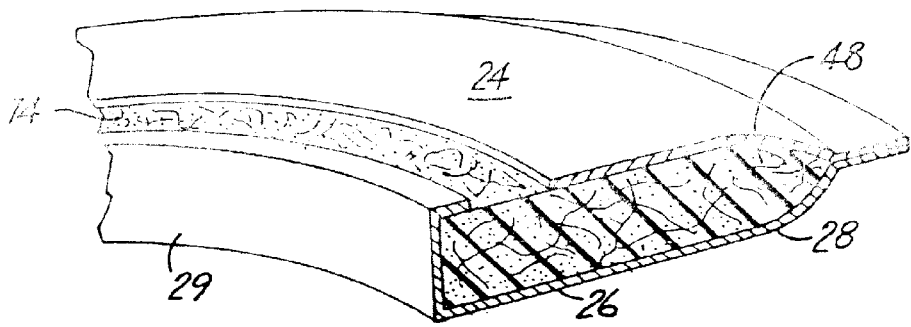
FIG. 9b is a fragmentary perspective view of another embodiment of the present invention.
Figure 10:
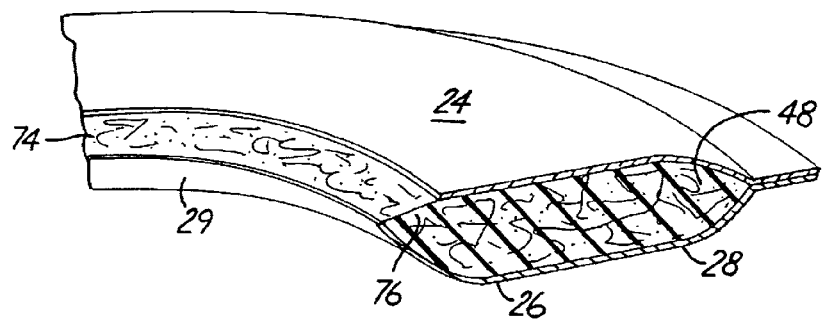
FIG. 10 is a fragmentary perspective view of another embodiment of the present invention.

FIG. 7, and FIGS. 8–10, depict embodiments of the present invention wherein the walls of the plenum 28 defining the access opening or aperture is an open facing 74, and wherein the open facing 74 extends into the top wall 24 of the plenum 28. As shown in FIGS. 7 and 8, the access opening wall is substantially completely an open facing 74 which extends upwardly at an angle or bevel 76 into the top wall. The bias or angle into the top wall may be from 10 to 60 degrees, with 45 degrees well-suited for many procedures. FIGS. 9a and 9b depict two unbeveled embodiments, and FIG. 10 depicts an embodiment wherein the inside wall of the plenum 28 is substantially continuous, only the bevel 76 comprising the open facing portion of the plenum 28. These embodiments generally are well-suited for use in surgical procedures involving a flap or ridge of tissue which, if the top wall or a portion thereof was not adapted to provide an intake for gaseous material, might occlude the open facing, blocking or at least interfering with the flow of the gaseous material into the plenum 28. The embodiment depicted in FIG. 10 may be further adapted for particular surgical procedures, such as procedures involving the breast, by providing a sealing means, such as an adhesive, on the inside rim or wall 29 of the plenum 28 so it can be adhered or sealed in place to the breast with a portion of the breast extending through the access opening.

Figure 11:
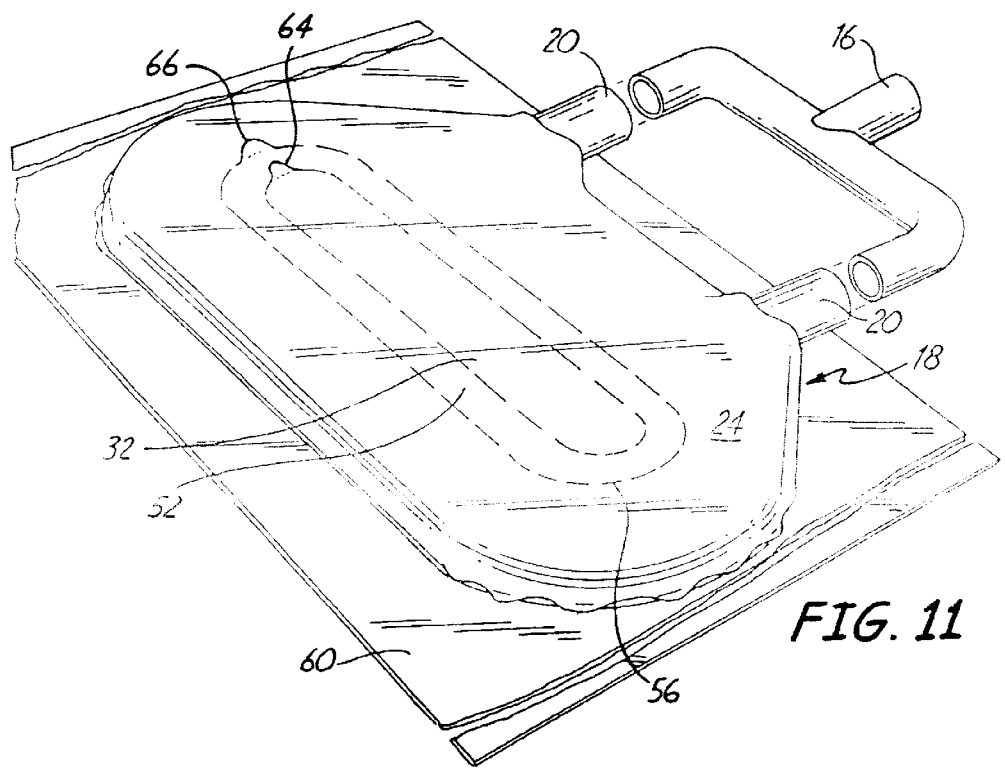
FIG. 11 is a perspective view of another embodiment of the present invention.

FIG. 11 depicts a drape/smoke evacuator embodiment of the present invention wherein dual vacuum coupling attachment handles are provided. Such an embodiment may be well-suited for procedures requiring large incisions, such as spinal procedures, thoracotomy, large abdominal incisions and the like. In one embodiment, the evacuator embodiment of FIG. 11 may be used as a stand alone device without a drape as depicted in FIG. 11.

Figure 13:
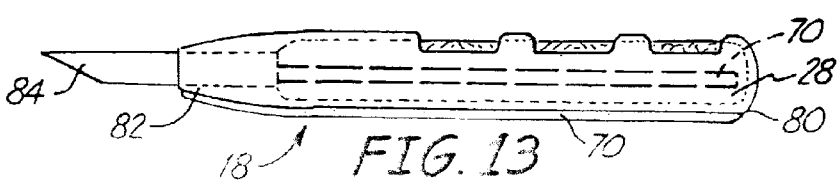
FIG. 13 is a perspective view of another embodiment of the present invention.
Figure 14:
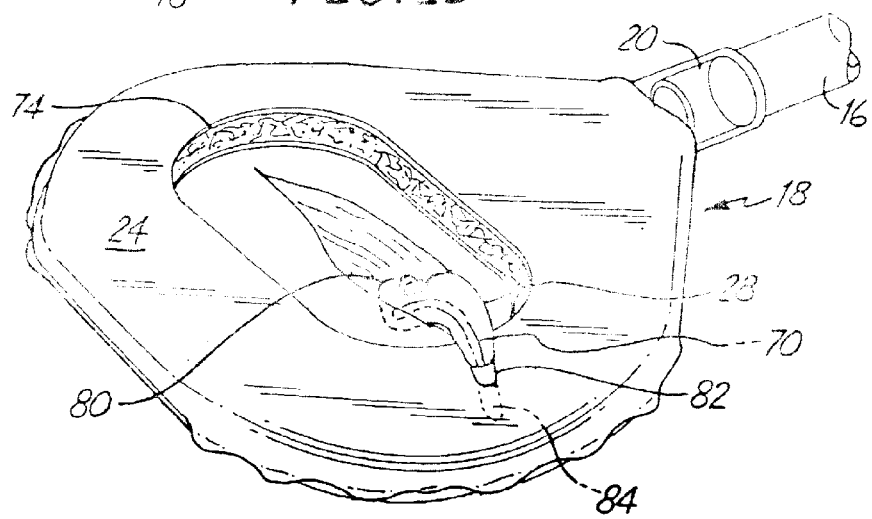
FIG. 14 is a perspective view of another embodiment of the present invention.

FIGS. 13 and 14 depict another embodiment of the smoke evacuator of the present invention wherein the plenum 28 is formed by a substantially continuous wall, which may be a single piece of extruded material or which may be formed from joined top, bottom and side walls. In this embodiment, the vacuum head 18 and the plenum 28 have a generally tubular, straight, elongated shape with two free ends, one end 80 of which may be closed and the other end 82 which may be adapted to be coupled to another embodiment of the end effector 18 of the invention, as shown in FIG. 14. The end 82 adapted to be coupled is provided with a sharpened, cannula-like member 84 for penetrating the wall of the plenum 28 as shown in FIG. 14. The end 82 may be flattened or otherwise adapted to be similarly attached to suction tubing or to the above described channel. In one embodiment (not shown), the cannula-like member 84 is not sharpened as depicted in FIG. 13. In other embodiments (not shown), this embodiment of the invention may be adapted for direct coupling to a hose or other fitting, or may include or be attached to a manifold or handle 20 generally similar to that shown in FIG. 1, for coupling to a hose or other fitting. Note that FIG. 14 also depicts that the stiffening skeletal member 70, shown in two of its possible locations, may be used to configure and position the generally tubular smoke evacuator 18 embodiment, or a portion thereof, in a relatively deep incision or wound.

Figure 15:
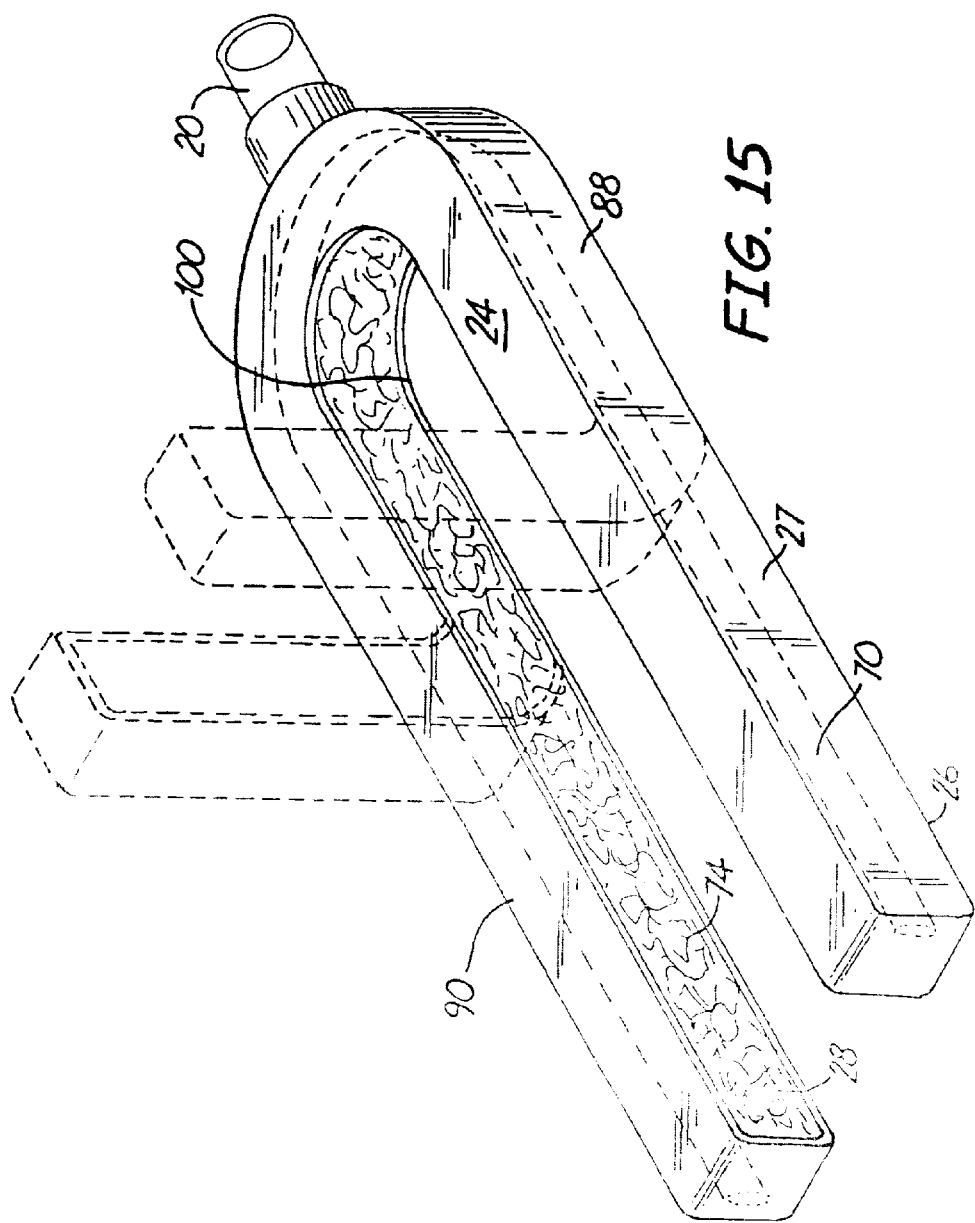
FIG. 15 is a perspective view of two embodiments of the present invention as they might be used in conjunction.

FIG. 15 depicts an embodiment of the smoke evacuator of the present invention adapted for spinal operations or other procedures wherein a relatively long incision may be used. The plenum 28 is formed in the shape of two generally parallel tubular members 88, 90, each having substantially continuous top, bottom, outside and end walls, and an inside wall comprising an open facing 74. Each embodiment of the invention may include a generally enlarged internal plenum space adjacent to the manifold port or handle 20. In the evacuator of FIG. 15, for example, the top wall 24 and bottom wall 26 are extended to form an enlarged plenum space 100 adjacent the manifold port or handle 20, such that the suction force generated at the manifold or handle 20 is more evenly dispersed, including throughout the plenum and along the open facing 74. Such a feature may be included in any of the embodiments of the invention described herein. Note that, as in all the embodiments described herein, the malleable, skeletal stiffening member 70, which might be formed of nitinol or similar "memory" material, may be incorporated to facilitate re configuring this embodiment to, for example, the configuration shown in phantom. This embodiment of the vacuum head 18 may have a single connection manifold or nozzle 20 as shown, or it may be adapted to have two manifolds with a circuit adapter to permit them both flow into a single ⅞" vacuum hose (see, for example, FIG. 11). Such circuit adapters are readily available as standard catalog items for respiratory therapy and anaesthesia.

Figure 16:
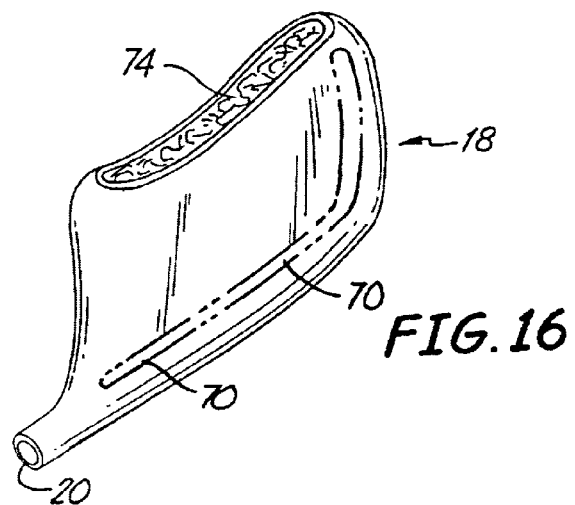
FIG. 16 is a perspective view of another embodiment of the present invention.

FIG. 16 depicts an embodiment of the smoke evacuator 18 well-suited for use in dental surgery, e.g., a "bite-block" embodiment. It should be appreciated that the smoke evacuator 18 maybe provided in any configuration suitable for use in or around the mouth, and that substantially the entire skin or walls forming this embodiment would preferably be non-absorbent.

Figure 17:
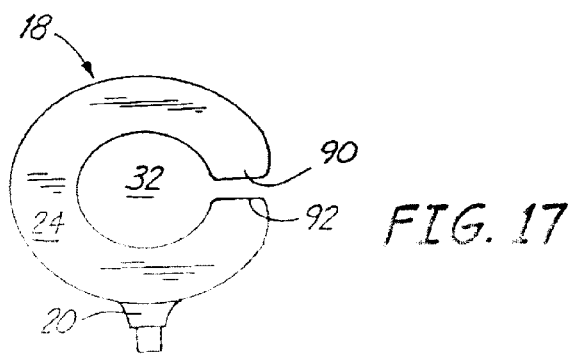
FIG. 17 is a perspective view of another embodiment of the present invention.
Figure 18:
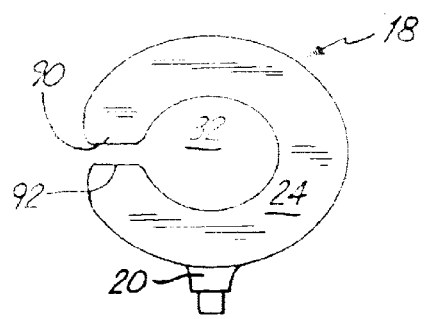
FIG. 18 is a perspective view of another embodiment of the present invention.

FIGS. 17 and 18 depict an embodiment wherein a generally tubular vacuum head 18 comprises an internal plenum region adjacent to the manifold port or handle 20 and two plenum arms 90, 92. The two plenum arms 90, 92, which, as in FIGS. 17 and 18, may be two free arms, may be curled or curved to substantially surround a surgical site. An advantage of this embodiment is that the plenum arms 90, 92 with their free end are flexible, whereby the head 18 is made more flexible so it may more easily assume and conform to the shape of the underlying tissue. The arms 90, 92, and thus the head 18, may move in various directions according to the layout of adjacent tissues. Because, in one embodiment, one surface of the vacuum head 18 of FIGS. 17 and 18 may have an adhesive attached thereto for attachment to a drape, it may be desirable to have one embodiment wherein the ends 90, 92 face one direction when viewed from the top and another embodiment wherein the ends 90, 92 face the other direction. These embodiments may provide for the flexibility needed for various surgical procedures, including procedures on bilateral, mirror image structures or tissues.

FIGS. 19a–g depict embodiments of the smoke evacuator 18 which can be used for creating unidirectional and/or laminar flow of ultra-clean air or other gas or fluid through or over a work site. These embodiments of the present invention provide a laminar or balanced airflow and evacuation and/or filtration system. In these embodiments, the inflow rate of ultra-clean air or other gas may be at a steady rate, a variable rate, or pulsed.

Figure 19A:
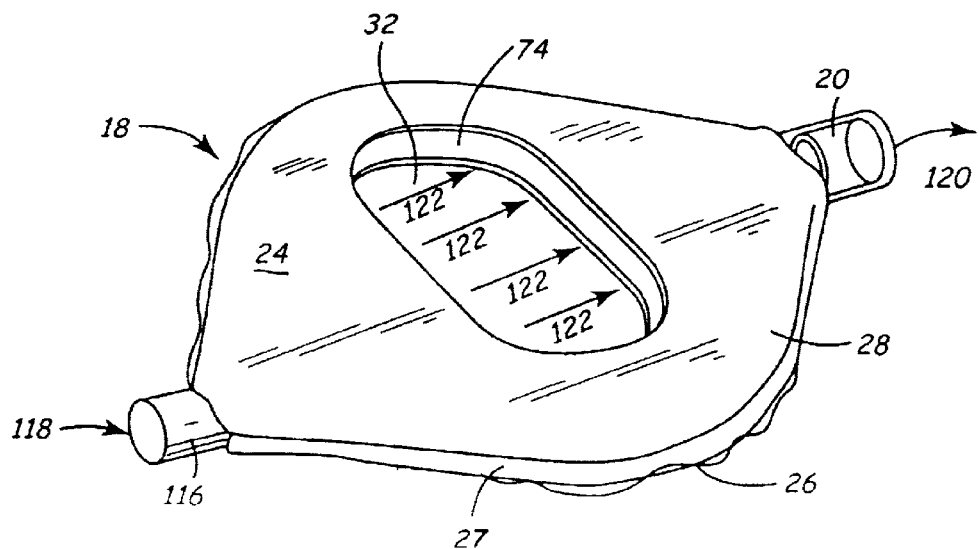
FIG. 19a is a perspective view of another embodiment of the present invention.

In one embodiment, as shown in FIG. 19a, the evacuator 18 comprises a plenum 28 having a central opening 32, a plenum support 74 for preventing the plenum from collapsing or expanding when a flow, high pressure, vacuum, or low pressure is established therein, and is adapted to facilitate the delivery of a fluid, e.g., ultra-clean air, across or in the central opening 32 of the evacuator 18. In one embodiment, the evacuator 18 employs two coupling attachment handles 20 and 116. One of the attachment handles 20, acting as an outlet, could be attached to a low pressure, or vacuum source. The other attachment handle 116, acting as an inlet, could be attached or hooked up to a source of ultra-clean air or other gas, including a high pressure source.

The ultra-clean air could be blown under pressure into the evacuator 18 through the attachment handle 116 as shown by arrow 118. The inflow of ultra-clean air or other gas, may be at a steady rate, a variable rate, or a pulsed rate. In an embodiment where ultra-clean air flows in at a steady rate, the plenum support 74 could act to evenly distribute the air so that a generally uniform, unidirectional laminar flow of the air would flow through the aperture 32 and over the surgical work site as shown by arrows 122. The vacuum source, pulling air through the attachment handle 20 could act to pull the ultra-clean air through the evacuator 18, and into a filter, as shown by arrow 120. In some embodiments, particularly those in which the central opening 32 is small, the pressurized source of ultra-clean air may be sufficient to create a substantially laminar flow of ultra-clean-air in the central opening 32, and into a suitable passive exhaust system, including a passive filtration system, such as that described in U.S. Pat. No. 6,110,259, the disclosure of which is incorporated herein by reference. In other embodiments, a "pull" could be used to establish an airflow, i.e., a vacuum source could draw air into and through the central opening 32. In other embodiments, a "push/pull" arrangement could be used, wherein a fluid, e.g., ultra-clean air or a mixture of ultra-clean air and another gas or fluid, would be supplied through the inlet 116 by pressure, and withdrawn through the outlet 20 by a vacuum. In these embodiments, it is preferable that the outflow is greater than or equal to, the inflow. This helps the invention to act as an effective evacuation device by preventing a buildup of the inflow fluid in the central opening 32. In any embodiment, suitable pre or post plenum filters may be used. In other embodiments, other types of gases may be blown through the plenum 28, such as an inert gas, or oxygen, depending on what the situation requires.

The present embodiment could be self contained or incorporated into a surgical drape. The present embodiment could also have: a central aperture 32 of various shapes and sizes, limited only by the requirement of having a sufficiently high air pressure and/or low air pressure to maintain a controlled, unidirectional airflow velocity completely across the opening 32. The coupling attachment handles 20, 116 could couple to the air pressure sources via standard surgical tubing or other flexible forms of tubing.

An advantage of these embodiments is that a laminar airflow of ultra-clean air has been shown to act as an additional measure against surgical site infection risk for certain procedures. The embodiment is designed to move particle-free air (called ultra-clean air) over the aseptic operating field at a uniform velocity. The laminar airflow may act as a barrier to and may sweep away contaminants, e.g., bacteria, and particles in its path, and those particles could then be sucked into a filter via the vacuum source.

Figure 19B:
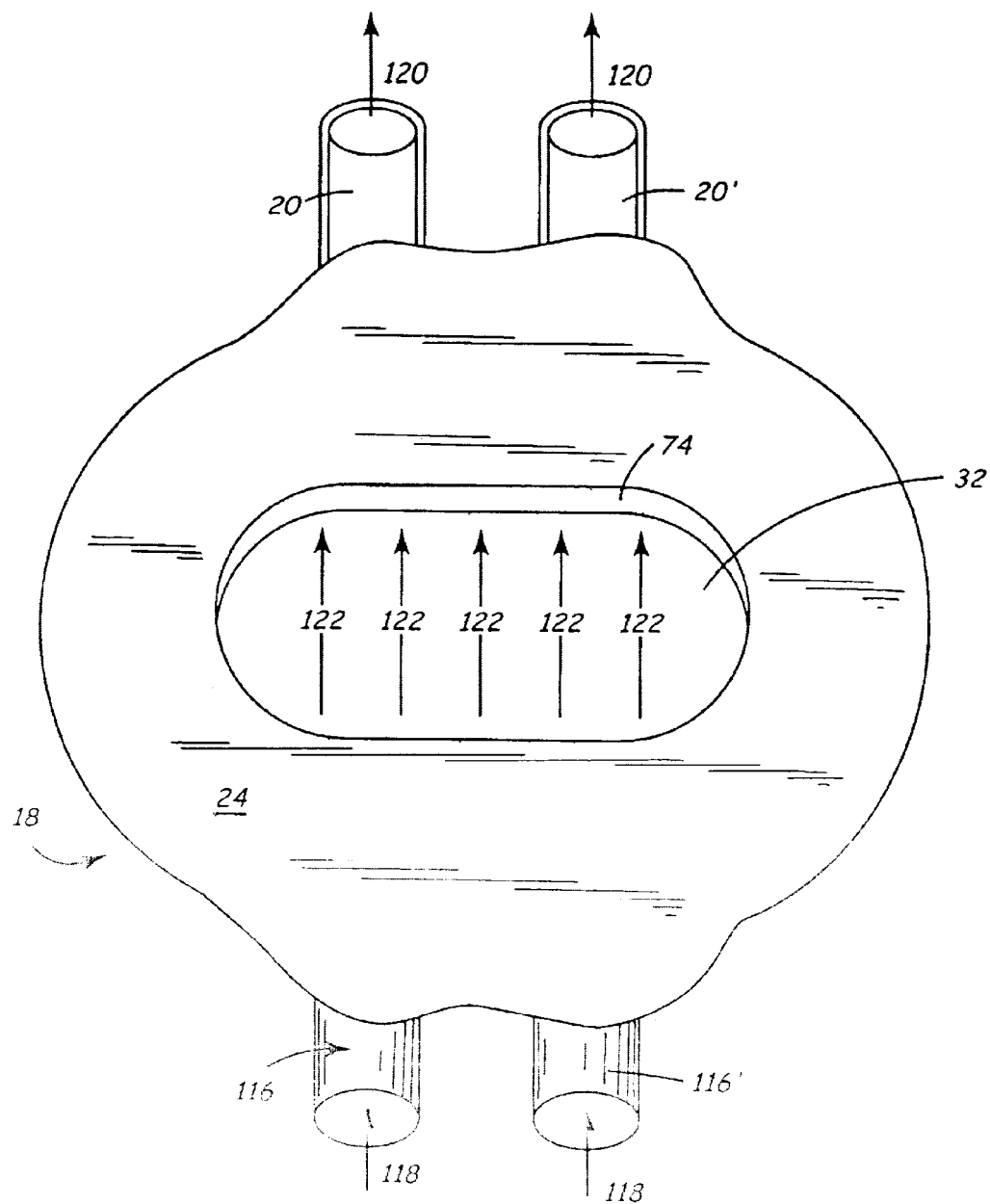
FIG. 19b is a perspective view of another embodiment of the present invention.

FIG. 19b shows an alternative embodiment of FIG. 19a, where multiple inlet and outlets are available for a ultra-clean air source and a vacuum source. In this embodiment, two attachment handles 116, 116' are provided on one side for coupling to a fluid source, e.g., ultra-clean air, and two attachment handles 20, 20' are provided on the other side of the plenum for coupling to a vacuum. This type of head could be useful in situations where the surgical site is quite large, like a large incision on the back. This embodiment would also be well suited for using a mixture of two different fluids to flow to the plenum. The attachment handles 116, 116' could be adapted to separately couple to each fluid source.

Figure 19C:
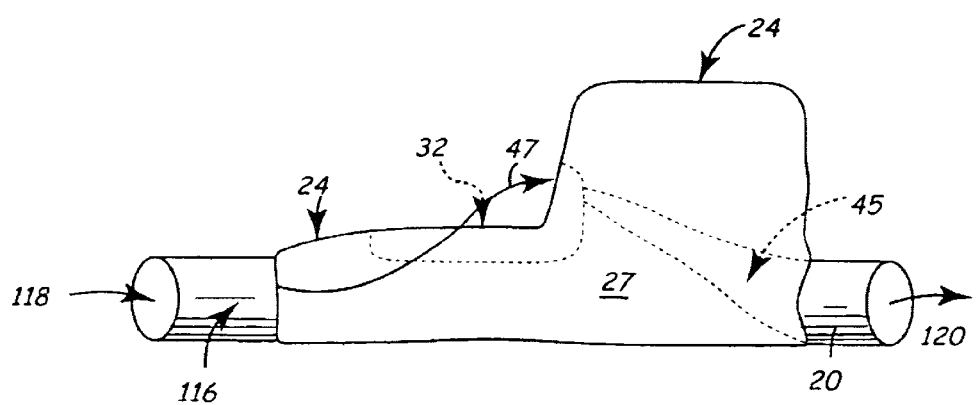
FIG. 19c is a side view of another embodiment of the present invention.

Other variations of the invention shown in FIGS. 19a and b are possible, such as more attachment handles on one side than the other, or one side of the plenum could be thicker than the other as shown in FIG. 19c. In FIG. 19c, one side of the top of the plenum 24' is at a higher level than the other side of the top of the plenum 24". In this variation, the pathways from the inlets and outlets into or out of the central opening may be manipulated in order to create a desired fluid flow profile. One possible passageway 45 is shown in phantom in FIG. 19c creating a fluid flow profile 47. This could create a better distribution of the airflow, either out of the fluid source, or into the vacuum.

Figure 19D:
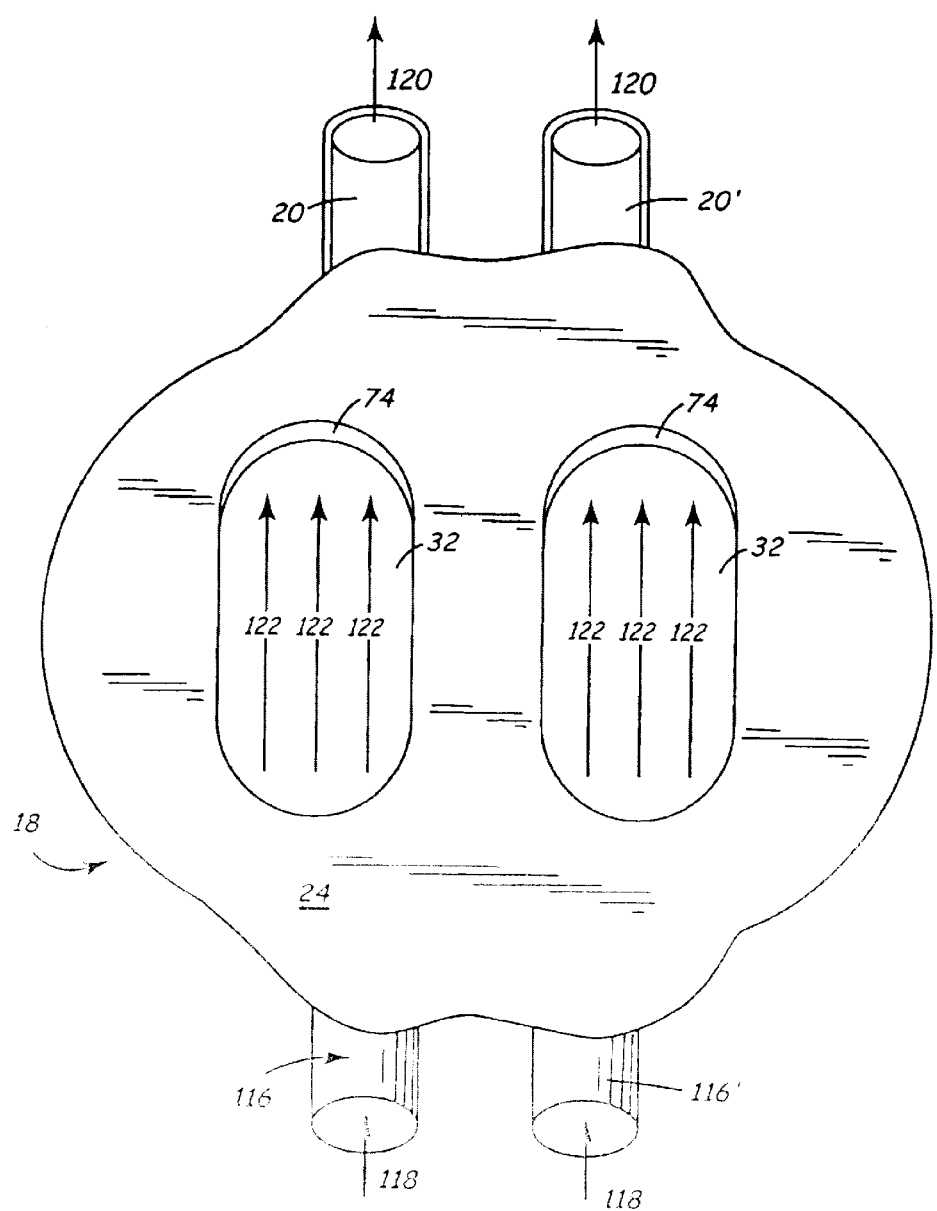
FIG. 19d is a perspective view of another embodiment of the present invention

In another variation of FIGS. 19a and 19b, there could be more than one central opening, as shown in FIG. 19d. In another variation, the plenum 28 may have a different shape in order to better conform with its work area and/or to shape the airflow.

Figure 19E:
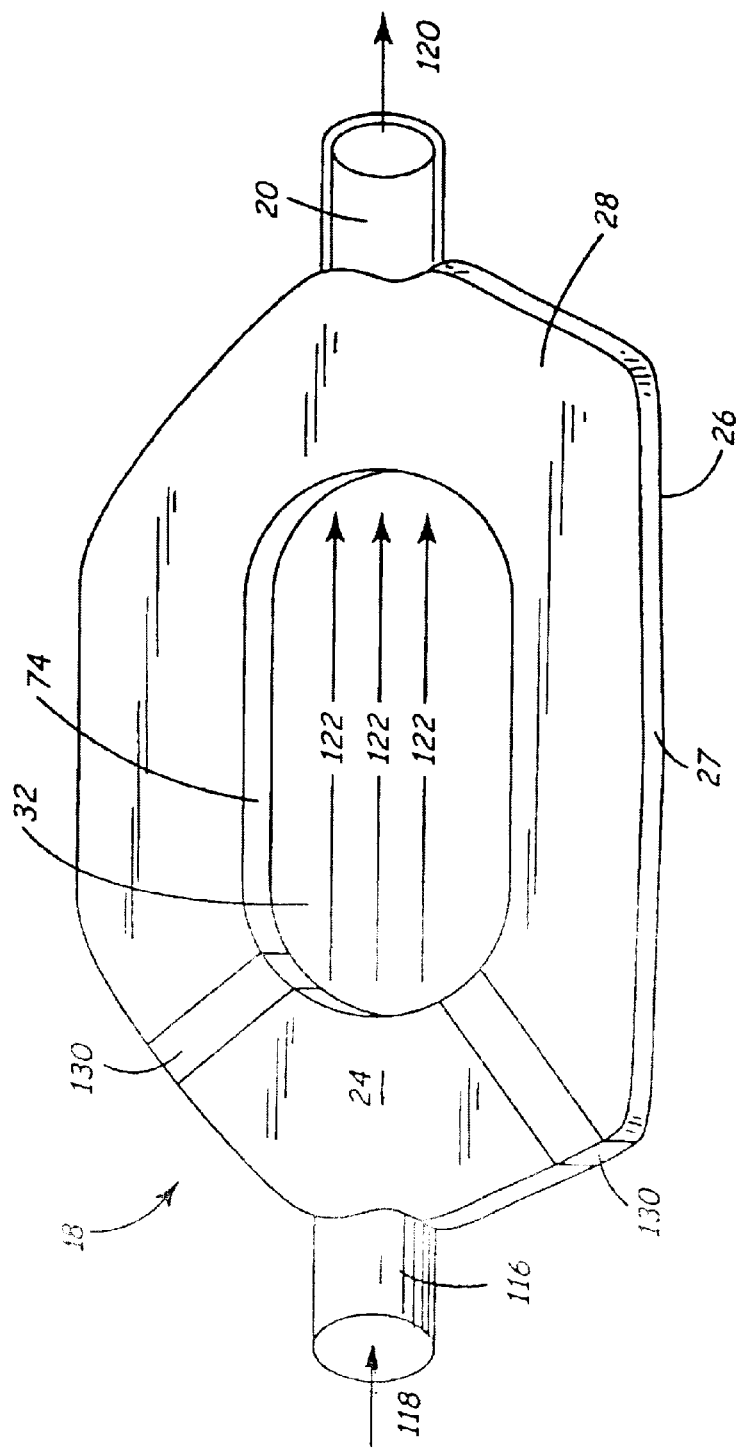
FIG. 19e is a perspective view of another embodiment of the present invention.

One embodiment of the present invention, as shown in FIG. 19e, could include manifolds 130 to preferentially direct the airflow to a specific portion of the central aperture 32. The manifolds 130 can be constructed to join the top and the bottom of the plenum, and may be solid or perforated. The manifolds 130 can act to prevent the airflow from diffusing in all directions as it enters from the inlet 116, by helping to concentrate and direct the flow through the central aperture 32, towards the outlet 20. In one embodiment, the preferential direction of the airflow out of the inlet 116 and into the central aperture 32 subtends or transverses an arc of approximately 5°, but is less than approximately 180°. In another embodiment, the manifolds 130 can act to direct the airflow so that the airflow covers at the most, the central half of the skin surface area exposed in the central aperture 32. An advantage of the manifolds 130 is that they help to direct the airflow more directly and evenly over the surgical site. Without the manifolds 130, a portion of the airflow may diffuse into and through the plenum support 74, effectively flowing around the surgical site. Also, at certain times, objects will be in the central aperture 32, such as a surgeon's hand, or an instrument when making a retraction. Without manifolds, the airflow will take a path of least resistance, which may be into the plenum support 74 and around the central aperture 32. In these situations, manifolds 130 will force the airflow to the central aperture 32, so that the airflow can still effectively sweep away particles or plumes.

Figure 19F:
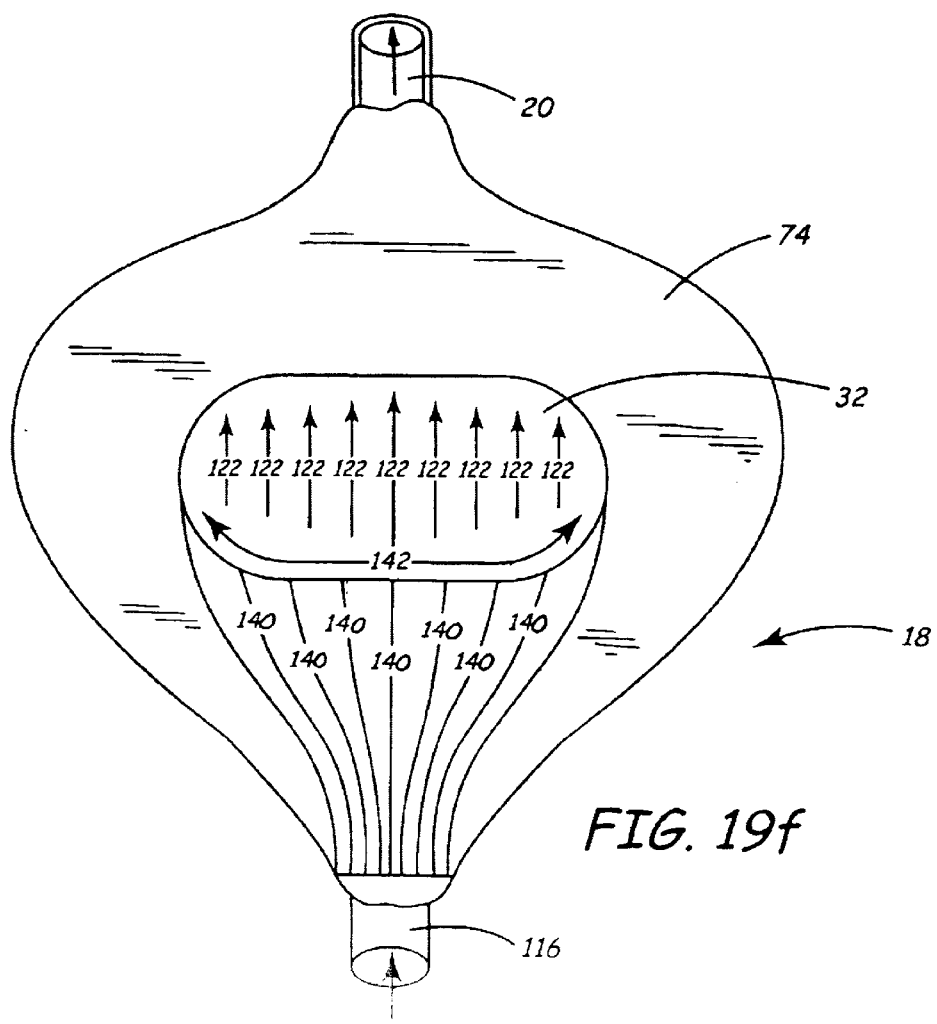
FIG. 19f is a top view of another embodiment of the present invention with the top material of the plenum removed.
Figure 19G:
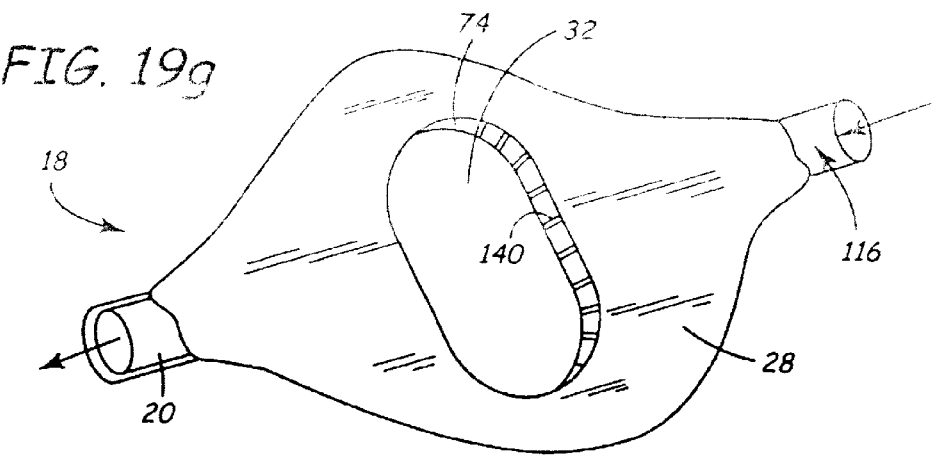
FIG. 19g is a perspective view of the embodiment of the present invention shown in FIG. 19f.

In another embodiment, as shown if FIGS. 19f and 19g, baffles 140 can be used to have a plenum in which the laminar flow of air is balanced across the central opening 32. FIG. 19f shows the embodiment from a top view with the top part of the plenum removed in order to see the inner construction. In this embodiment, one or more baffles 140 can be set in the plenum support area between the inlet port 116 and the central aperture 32. The baffles 140 can help to separate and direct the airflow into lanes or channels so that a consistent air velocity is achieved across the entire edge 142 of the central aperture 32. In this embodiment, the input 116 and output 20 ports can have varying sizes in order to help achieve a balanced airflow across the central aperture 32. FIG. 19g shows a perspective view of the embodiment described above as it could be used.

In use, it should be understood that operation of all the embodiments disclosed herein may be generally similar. The vacuum head 18, or the drape 60 with the vacuum head 18 integrated, is detachably affixed to the skin surrounding a surgical site by peeling off the sterile peel-off shield 46 and pressing the adhesive layer 44 carried by the bottom wall 26 of the body 22 against the skin. It will be appreciated that the flexible vacuum head 18 permits a complete, airtight seal of the bottom wall 26 against the skin or any skin covering (such as a clear drape). The films 28, 42 carried by the top and bottom walls 24, 26, respectively, can be entirely removed. Upon actuation of the vacuum source 14, air is drawn into the plenum 28, and is transported through the flexible hose 16 and into the filter (not shown) in the vacuum source 14. The porous plenum support 48 carried within plenum 28 prevents plenum 28 from collapsing under the influence of the vacuum. The plenum support 48 also may be adapted to enhance the effect of diffusing the vacuum around or through the plenum 28, thereby enhancing the drawing air into the plenum 28 around its entire periphery or open facing, rather than solely in the vicinity of handle 20. Moreover, drawing air through the larger opening presented by the plenum 28 reduces the noise created by the flow of air into hose 16. Gaseous or aerosol material produced at the surgical site is thereby drawn into the plenum 28 and evacuated through flexible hose 16. The plenum support 48, due to its porous nature, also may act as a filter as the smoke is drawn through it, and/or specific filtration media may be integrated with the support 48.

Referring back to FIG. 1, surgical instruments can be manipulated through the tear line T in clear film 38 and/or through the access opening 32. Alternatively, the clear film 38 can be completely removed. It will be appreciated that the vacuum, and drawing effect, presented by the plenum 28 to the surgical site may be increased by leaving the clear film 38 in place.

The end effector(s) 18 of the present invention may be extruded from a single piece of material, e.g., the body 22, tubular handle 20, flexible hose 16, and in some embodiments, a filter and connector, may be formed from a unitary piece of synthetic resin or similar extrudable material. The end effector(s) 18 of the present invention may be advantageously and hygienically disposed of after a single use, without the necessity of handling contaminated material.

Figure 20:
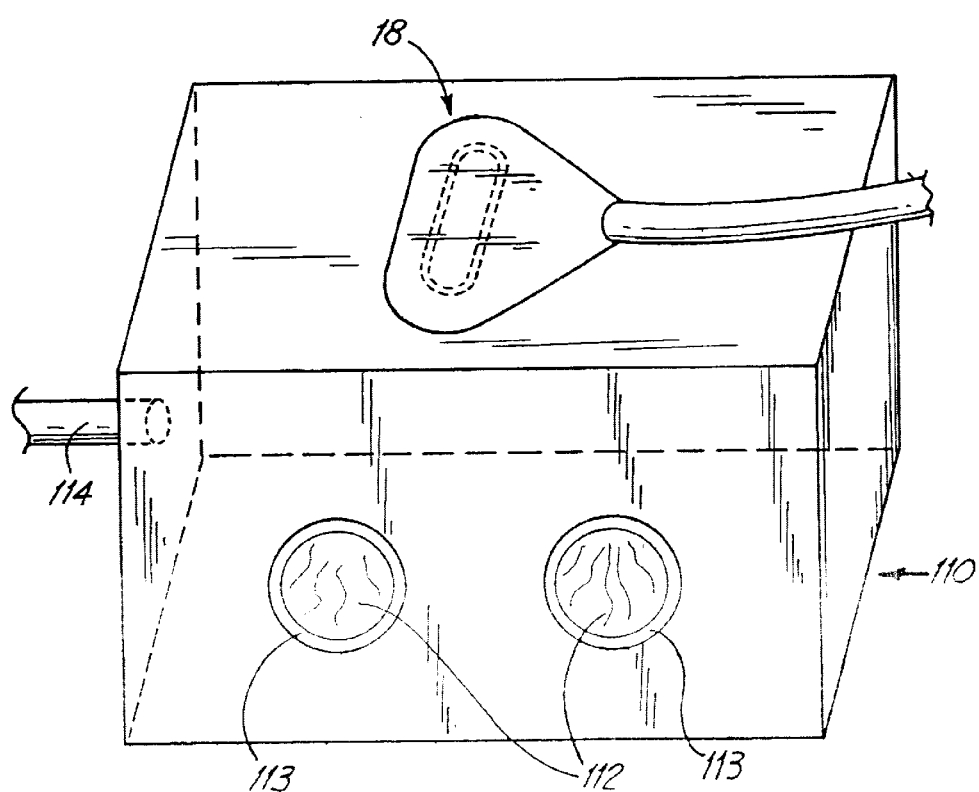
FIG. 20 is a perspective view of an embodiment of the invention in use in a workstation.

In another use of the invention, the embodiments of the vacuum head 18 may be used at a workstation or the like, or on or in a containment vessel or the like, in order to remove fumes or smoke. Such workstations and vessels may be used, for example, for cleaning components in the computer industry or for performing experiments or tasks in which noxious fumes are emitted. FIG. 20 shows such a use. The workstation 110 may have hand holes 112, with or without suitable sealing collars 113 or attached gloves (not shown), through which a technician or user may put their gloved or ungloved hands. The vacuum head 18 may be positioned in, adjacent to or on the workstation 110, for example, as depicted, it may be coupled to an exterior surface of the workstation enclosure adjacent to an opening in the wall defining the workstation. It may also be coupled to an interior surface. When a suction force is applied to the vacuum head 18, the vacuum head 18 receives smoke or fumes from the inside of the workstation. In one embodiment, an air supply, or supply of ultra-clean air and/or other gases, may be pumped into the workstation 110 through a hose 114 to help urge the vapors, aerosols or gaseous material toward the vacuum head 18. Such an air supply may provide air at any given rate; one such rate for a typical-sized work station may be 30 cubic feet per minute.

One embodiment is a method for removing fumes or smoke from a workspace, where a vacuum head as described above in several different embodiments can be used. The head substantially defines a plenum having an inner periphery defining a generally central opening, and has a generally open facing adjacent to the inner periphery. The plenum has a plenum support for preventing the plenum from collapsing when a low pressure is established therein. A user places the vacuum head in or around the workspace, couples the head to a vacuum source, and actuates the vacuum source, providing an evacuation system for fumes and smoke. Optionally, the vacuum head may also be operably coupled to a fluid source, such as ultra-clean air, or an inert gas, or combinations thereof, in order to create a flow of the fluid into the head and across the central opening.

The present invention may be embodied in other specific forms without departing from the essential spirit or attributes thereof. The described embodiments should be considered in all respects as illustrative, not restrictive.

What is claimed is:

1. An evacuation apparatus for removing gaseous byproducts or noxious vapors comprising:
   a head operatively coupled to a vacuum and a fluid source, said head substantially defining a plenum having an outer surface, said plenum having an inner periphery defining a generally central opening, said plenum having an opening in said outer surface adjacent to the inner periphery; and
   a plenum support for preventing the plenum from collapsing when a low pressure is established therein,
   wherein said head is operatively coupled to said fluid source with at least one nozzle, and operatively coupled to said vacuum with at least one nozzle, wherein said at least one nozzle operatively coupled to said fluid source and said at least one nozzle operatively coupled to said vacuum are generally opposed.

2. The evacuation apparatus according to claim 1, further comprising at least a plurality of manifold barriers carried by said plenum, wherein said manifold barriers cover a portion of said inner periphery adjacent to said one nozzle operatively coupled to said fluid source.

3. The evacuation apparatus according to claim 2, wherein said manifold barriers are solid.

4. The evacuation apparatus according to claim 2, wherein said manifold barriers are perforated.

5. The evacuation apparatus according to claim 1, wherein said fluid source supplies generally particle-free air to said head.

6. The evacuation apparatus according to claim 1, wherein a generally unidirectional, laminar airflow runs through said central opening in the general direction of said vacuum.

7. The evacuation apparatus according to claim 1, further comprising at least one baffle located in said plenum between said nozzle operatively coupled to said fluid source and said central opening.

8. The evacuation apparatus according to claim 1, further comprising a piece of sheet material, said apparatus operably coupled to said piece of material.

9. An evacuation apparatus for removing gaseous byproducts or noxious vapors comprising:
 a head operatively coupled to a vacuum and a fluid source, said head substantially defining a plenum having an outer surface, said plenum having an inner periphery defining a generally central opening, said plenum having an opening in said outer surface adjacent to the inner periphery; and a plenum support for preventing the plenum from collapsing when a low pressure is established therein, wherein said plenum has a bottom wall, wherein said bottom wall of said plenum includes an adhesive layer for adhesive attachment of said head around a surgical site.

10. The evacuation apparatus according to claim 9, wherein said plenum is constructed of a generally non-porous material.

11. The evacuation apparatus according to claim 9, wherein said plenum support is constructed of a generally porous material.

12. The evacuation apparatus according to claim 9, wherein said fluid source supplies an inert gas through said head.

13. A medical appliance comprising a working head having a central opening for at least partially surrounding a surgical site and said working head operably coupled to a vacuum source and a source of clean air, said working head including at least one inlet connectable to the source of clean air and at least one outlet connected to the vacuum source, whereby actuation of at least the vacuum source produces an air flow of clean air through the central opening and over the surgical site.

14. The medical appliance according to claim 13, wherein said air flow is laminar.

15. The medical appliance according to claim 13, wherein said working head defines a plenum having an outer surface, said plenum having an opening in said outer surface adjacent to an inner periphery of said central opening of said plenum.

16. The medical appliance according to claim 15 further comprising a plurality of manifold barriers carried by said plenum, wherein said manifold barriers cover a portion of said inner periphery adjacent to said at least one inlet.

17. The medical appliance according to claim 13, wherein said working head substantially contains air flow when actuation of the vacuum source occurs.

18. The medical appliance according to claim 13, wherein said at least one inlet and said at least one outlet are on generally opposite sides of said working head.

19. The medical appliance according to claim 15, further comprising at least one baffle located in said plenum between said at least one inlet and said at least one central opening.

20. A method for removing fumes from a workspace, comprising;
 providing the workspace;
 providing a head, said head substantially defining a plenum having an outer surface, said plenum having an inner periphery defining a generally central opening, said plenum having an opening in said outer surface adjacent to the inner periphery, said plenum having a plenum support for preventing the plenum from collapsing when a low pressure is established therein;
 providing a vacuum source;
 providing a source of ultra-clean air;
 coupling said head and said vacuum source;
 coupling said head to a connection point of said source of ultra-clean air; and
 actuating said vacuum source and said source of ultra-clean air, whereby fumes are removed from the workspace.

21. The method according to claim 20, said head further comprising a plurality of manifold barriers carried by said plenum, wherein said manifold barriers cover a portion of said inner periphery adjacent to said connection point of said source of ultra-clean air.

22. A method for removing fumes from a workspace, comprising;
 providing the workspace;
 providing a head, said head substantially defining a plenum having an outer surface, said plenum having an inner periphery defining a generally central opening, said plenum having an opening in said outer surface adjacent to the inner periphery, said plenum having a plenum support for preventing the plenum from collapsing when a low pressure is established therein;
 providing a vacuum source;
 coupling said head and said vacuum source;
 actuating said vacuum source, whereby fumes are removed from the workspace;
 providing a fluid source, and operably coupling said head and said fluid source at a fluid source connection point;
 actuating said fluid source to provide a flow of fluid to said head, wherein said head further comprises at least one baffle located in said plenum between said fluid source connection point and said central opening.

23. The method of claim 22, wherein at least a portion of said fluid comprises an inert gas.

24. The method of claim 22, wherein said fluid is ultra-clean air.

25. An evacuation apparatus for removing gaseous byproducts or noxious vapors comprising:
 a head operatively coupled to a vacuum and an ultra clean fluid source, said head substantially defining a plenum having an outer surface, said plenum having an inner periphery having a generally central opening defining a 360 degree arc, said plenum having an opening in said outer surface adjacent to the inner periphery so that laminar air flow from the ultra-clean fluid source and the vacuum act together to evacuate gaseous material across an area defined by the 360 degree arc; and
 a plenum support for preventing the plenum from collapsing when a low pressure is established therein.

26. The evacuation apparatus according to claim 25, wherein said head is operatively coupled to said fluid source with at least one nozzle, and operatively coupled to said vacuum with at least one nozzle, wherein said at least one nozzle operatively coupled to said fluid source and said at least one nozzle operatively coupled to said vacuum are generally opposed.

27. The evacuation apparatus according to claim 26, further comprising at least one baffle located in said plenum between said nozzle operatively coupled to said fluid source and said central opening.

28. The evacuation apparatus according to claim 25, wherein said fluid source supplies generally particle-free air to said head.

29. The evacuation apparatus according to claim 25, further comprising a piece of sheet material, said apparatus operably coupled to said piece of material.

30. The evacuation apparatus according to claim 25, wherein said plenum has a bottom wall, wherein said bottom wall of said plenum includes an adhesive layer for adhesive attachment of said head around a surgical site.

31. The evacuation apparatus according to claim 25, wherein said plenum is constructed of a generally non-porous material.

32. The evacuation apparatus according to claim 25, wherein said plenum support is constructed of a generally porous material.

33. The evacuation apparatus according to claim 25, wherein said fluid source supplies an inert gas through said head.

34. A medical appliance comprising a working head having a central opening for being positioned around a surgical site, the working head operably coupled to a vacuum source and a source of clean air, said working head including at least one inlet connectable to the source of clean air and at least one outlet connected to the vacuum source, whereby actuation of the vacuum source and the source of clean air produces a laminar flow of clean air through the central opening and over the surgical site, wherein an inflow of the vacuum source is greater than or equal to an outflow of the source of clear air including any gaseous materials removed.

35. The medical appliance according to claim 34, further comprising at least one baffle located in said working head between said at least one inlet and said central opening.

36. The medical appliance according to claim 34, wherein said working head substantially contains air flow when actuation of the vacuum source occurs.

37. The medical appliance according to claim 34, wherein said at least one inlet and said at least one outlet are on generally opposite sides of said working head.

38. An evacuation apparatus for removing gaseous byproducts or noxious vapors comprising:
   a head operatively coupled to a vacuum and an ultra-clean fluid source, said head substantially defining a plenum having an outer surface, said plenum having an inner periphery having a generally central opening surrounding a surgical site and through which the ultra clean fluid source provides a laminar air flow wherein an outflow of the ultra-clean fluid source is less than or equal to an inflow of the vacuum, said plenum having an opening in said outer surface adjacent to the inner periphery; and
   a plenum support for preventing the plenum from collapsing when a low pressure is established therein,
   wherein said head is operatively coupled to said fluid source with at least one nozzle, and operatively coupled to said vacuum with at least one nozzle, wherein said at least one nozzle operatively coupled to said fluid source and said at least one nozzle operatively coupled to said vacuum are generally opposed.

39. The evacuation apparatus according to claim 38, further comprising at least one baffle located in said plenum between said nozzle operatively coupled to said fluid source and said central opening.

40. The evacuation apparatus according to claim 38, further comprising a piece of sheet material, said apparatus operably coupled to said piece of material.

41. An evacuation apparatus for removing gaseous byproducts or noxious vapors comprising:
   a head operatively coupled to a vacuum and an ultra-clean fluid source, said head substantially defining a plenum having an outer surface, said plenum having an inner periphery having a generally central opening surrounding a surgical site and through which the ultra clean fluid source provides a laminar air flow wherein an outflow of the ultra-clean fluid source is less than or equal to an inflow of the vacuum, said plenum having an opening in said outer surface adjacent to the inner periphery; and
   a plenum support for preventing the plenum from collapsing when a low pressure is established therein,
   wherein said plenum has a bottom wall, wherein said bottom wall of said plenum includes an adhesive layer for adhesive attachment of said head around a surgical site.

42. The evacuation apparatus according to claim 41, wherein said plenum is constructed of a generally non-porous material.

43. The evacuation apparatus according to claim 41, wherein said plenum support is constructed of a generally porous material.

44. The evacuation apparatus according to claim 41, wherein said fluid source supplies an inert gas through said head.

* * * * *